(12) United States Patent
Charnock-Jones et al.

(10) Patent No.: US 6,472,374 B1
(45) Date of Patent: Oct. 29, 2002

(54) ENDOMETRIAL FUNCTION (75) Inventors: David Stephen Charnock-Jones; Stephen Kevin Smith; Andrew Mark Sharkey; Robert Brian Heap, all of Cambridge (GB)

(73) Assignee: Cambridge University Technical Services Limited, Cambridge (GB)

( * ) Notice: Subject to any disclaimer, the term of this patent is extended or adjusted under 35 U.S.C. 154(b) by 0 days.

(21) Appl. No.: 08/860,047

(22) PCT Filed: Dec. 21, 1995

(86) PCT No.: PCT/GB95/03008

§ 371 (c)(1),
(2), (4) Date: Sep. 18, 1997

(87) PCT Pub. No.: WO96/20013

PCT Pub. Date: Jul. 4, 1996

(30) Foreign Application Priority Data

Dec. 24, 1994 (GB) ................................................ 9426380
Oct. 12, 1995 (GB) ................................................ 9520879

(51) Int. Cl.[7] .......................... A61K 48/00; A61K 35/00

(52) U.S. Cl. ........................................ 514/44; 424/93.1

(58) Field of Search .......................... 514/44; 435/320.1, 435/455; 536/23.1, 23.52, 23.53, 24.5; 800/21; 424/93.1

(56) References Cited

U.S. PATENT DOCUMENTS 5,858,784 A * 1/1999 Debs et al. .................. 435/375

FOREIGN PATENT DOCUMENTS

| WO | 94 05782 | * 3/1994 | ........... C12N/15/00 |
| WO | 95 33050 | 12/1995 | |

OTHER PUBLICATIONS

Anderson, WF. Gene therapy for genetic disease. Human Gene therapy, vol. 5, pp. 281–282, 1994.*
Feldman, LJ et al. Prvention of restenosis after coronary angioplasty: towards a molecular approach? Fundam. Clin. Pharmacol., vol. 9, pp. 8–16, 1995.*
Ross, G et al. Gene therapy in the United States: a five–year status report. Human gene therapy, vol. 7, pp. 1781–1790, Sep. 10, 1996.*
Crystal, RG et al. Transfer of genes to humans early lessons and obstacles to success. Science, vol. 270, pp. 404–410, 1995.*
Yamada, H et al. Multiple chromosomes carrying tumor suppressor activity for a uterine endometrial carcinoma cell line identified by microcell–mediated chromosome transfer. Oncogene, vol. 5, pp. 1141–1148, 1990.*
Husband, AJ et al. Cytokine regulation of mucosal responses: a rational basis for new vaccine delivery strategies. Reprod. Fertil. Dev., vol. 6, pp. 381–388, 1994.*
Husband, et al: "Cytokine Regulation of Mucosal Responses: a Rational Bases for New Vaccine Delivery Strategies", Reproduction, Fertility and Development, vol. 6, No. 3, 1995, pp. 381–388, XP000566471.
Simon et al: "Embryonic Implantation in Mice is Blocked by Interleukin–1 Receptor Antagonist", Endocrinology, vol. 134, No.2, Feb. 1994, pp. 521–528, XP000566908.
Stewart et al: "Blastocyst Implantation Depends on Maternal Expression of Leukaemia Inhibitory Factor", Nature, vol. 359, Sep. 3, 1992, pp. 76–79.

* cited by examiner

Primary Examiner—Michael C. Wilson
(74) Attorney, Agent, or Firm—Pillsbury Winthrop LLP (57) ABSTRACT

Disclosed is a method of altering one or more characteristics of at least some of the cells of the reproductive tract of a mammalian individual by the introduction into said cells of a nucleic acid, together with a composition comprising nucleic acid, for use in the method.

10 Claims, 2 Drawing Sheets

ENDOMETRIAL FUNCTION

FIELD OF THE INVENTION

This invention relates, inter alia, to a method of altering one or more characteristics of mammalian endometrial tissue.

BACKGROUND OF THE INVENTION

Endometrial Physiology

Two major events are required for the embryo to become established in the mammalian uterus: firstly, the preparation of the endometrium so that it is receptive to the presence of a blastocyst which can then implant and acquire nutritive support through the formation of the placenta; and secondly, the modification of myometrial activity which must become quiescent and thereby allow the blastocyst to become resident within the uterine cavity without the danger of expulsion. Both these events are controlled by the action of the hormones of pregnancy, of which oestrogens and progesterone are particularly important. These steroid hormones act on the endometrium and myometrium through their receptors which are located in the nucleus of target cells. Once activated, the steroid-nuclear receptor complex interacts with specific regions within the DNA to stimulate, repress or de-repress genes that code for proteins and polypeptides such as enzymes or growth factors.

The initiation of implantation is brought about by a cascade of biochemical and biophysical changes. Adhesion molecules (e.g. CAM 105) have been implicated in the early stages of attachment of the blastocyst to the wall of the uterus. Afterwards, the blastocyst and endometrium adopt various stratagems to improve intimacy between fetal and maternal tissues. In ungulates, trophoblast cells which form the outermost layer of the blastocyst migrate into the uterine epithelium with which they subsequently fuse. Cell migration is carried a step further in women because it is not only isolated or specific cell types that migrate but large areas of trophoblast which insinuate between the uterine epithelial cells. In order to do this, some of the trophoblast cells fuse together to form a syncytium. The process is very rapid and the embryo becomes established in the uterine tissues without much apparent degeneration in the uterine epithelium. In some species the process of implantation is delayed, either to await environmental cues which ensure the young are born at favourable times of the year, or by physiological factors such as lactation so that the mother has finished weaning the previous litter before the next pregnancy becomes fully established.

The preparation of the uterus for implantation is regulated by the secretion of ovarian hormones. The transport of the fertilised egg through the oviduct has to be precisely timed so that it arrives in the uterus at the correct time of development and when the uterus is in a fit condition to receive it. Under most conditions the uterus is hostile to the embryo, more hostile in fact than some other areas of the body. The epithelial lining of the uterus is, under most conditions, resistant to attachment and invasion by trophoblast and it is only under very precise hormonal states that this resistance is relaxed.

In mice and rats unmated animals do not have a full oestrous cycle because they do not form a normal secretory corpus luteum which produces increasing amounts of progesterone. If mating occurs at oestrus, a time when high levels of oestrogens are secreted by the ovarian follicle from which the ovum is shed, a corpus luteum will form in the place of the ruptured follicle, rising concentrations of progesterone are then secreted, implantation occurs and pregnancy progresses (length, 21 days). If an infertile mating occurs, similar events occur except that the corpus luteum only lasts about 11 days and pseudopregnancy is curtailed.

The cellular and biochemical changes that take place in the endometrium have been most thoroughly studied in the mouse and the rat, though information about these aspects in women has increased substantially in recent years. The endometrium in all species is made up of three main tissues—luminal epithelium, glandular epithelium and stroma. Cell proliferation occurs at different times in the three tissues. Luminal cells proliferate just before oestrus (proestrus) under the influence of the rising levels of oestrogens produced by the follicles in the ovary. By day 1 of pregnancy (day of copulation plug in rodents) they have ceased division but then undergo a second, though smaller, burst of activity on day 3. Glandular cells show most activity on day 4 and then decline. Stromal cells do not proliferate until day 4 but thereafter, under the influence of progesterone, they reach high levels of proliferation by day 5. In women, less is known of these changes which presage the process of implantation but there appears to be peak proliferation in epithelial cells during the follicular phase of the cycle and in stromal cells during the luteal or secretory phase, as in the mouse and rat.

The purpose of endometrial cellular proliferation is not fully resolved. It is believed to prepare the endometrium for implantation by increasing the number of cells that will serve a nutritive and secretory function (glandular epithelium) and that participate in the very early stages of placentation (decidualization). As a prerequisite of successful implantation, cell mitosis may progress towards cellular differentiation and therefore plays a crucial role in the early events of the establishment of pregnancy. Evidence in support of this role is the endometrial production of growth factors (mitogens), cytokines and nuclear oncogenes. Many of these compounds are produced in increased concentrations in response to ovarian hormones acting through their receptors.

Amongst growth factors, much attention is currently given to epidermal growth factor (EGF), heparin binding epidermal growth factor (HBEGF), amphiregulin and insulin-binding growth factors (IGF-I and IGF-II). Evidence for the importance of the local (paracrine) action of at least one of these growth factors, amphiregulin, has been provided by recent experiments in mice. Inhibition of the implantation-specific and progesterone-regulated gene for amphiregulin was achieved by the anti-progestin, RU486, and this resulted in the prevention of implantation (Das et al. Molecular Endocrinology 9, 691–705, 1995).

Amongst the cytokines, leukaemia inhibitory factor (LIF) and colony-stimulating factor (CSF), which are also produced by the mouse uterus at the time of implantation, have been found from gene knockout studies to be indispensable, demonstrating that their removal is incompatible with implantation and normal placentation (Stewart et al. Nature 359, 76–79, 1992: Pollard et al. Developmental Biology 148, 273–283, 1991).

Amongst the nuclear oncogenes, levels of c-jun and c-fos (which are early indicators of gene transcription) increase in the uterus after oestrogen administration, and are inhibited by progesterone.

Important differences exist between various species in the extent of trophoblast invasion at the time of implantation. In women, the early trophoblast is highly invasive whereas in pigs, which have a non-invasive form of implantation, the endometrial epithelium is never breached throughout the three month gestation period. Failure of implantation in both these species is high, reaching about 60 and 30%, respectively. The reasons for this high rate of failure are complex and incompletely understood. In women, about half the loss is attributable to genetic abnormalities but in pigs, as in other ungulates where the loss is also high, genetic defects only account for a few percent of the total.

After implantation failure in women a fall in progesterone secretion causes bleeding, as at the end of the normal menstrual cycle; this does not occur in most other animals. Disorders of menstruation, as well as of implantation, are common. In addition menstrual bleeding, either as a consequence of sequential hormonal therapy, or in conjunction with continuous combined hormone replacement therapy or progestin-only long-acting contraceptives, is a significant cause of ill-health in women. The underlying reasons for this bleeding are the focus of many current studies into biochemical (e.g. prostaglandins, enzymes, polypeptides and proteins, vasoactive compounds such as platelet-activating factor PAF, and vascular endothelial growth factor VEGF) and cellular mechanisms (e.g. migrating cells homing to the uterus that produce immunosuppressive compounds).

Current understanding of reproductive processes largely centres on the control of steroid hormone production and the actions of these hormones on their target tissues. However paracrine and autocrine factors are increasingly seen to be key mediators of reproductive function, albeit interacting with steroids (Benton, 1991 Current Opinion in Cell Biology 3, 171–175: Rozengurt, 1992 Current Opinion in Cell Biology 4, 161–165; Tartakovsky et al., 1991 Developmental Biology 146, 345–352; Robertson et al., 1992 Current opinion in Immunology 4. 585–590; Smith, 1994 Human Reproduction 9, 936–946; and Tabibzadeh, 1994 Human Reproduction 9, 947–967). The clearest example of this is seen in the ovariectomized mouse. In this model the uterus undergoes marked growth in response to a single dose of estradiol. in this effect can be blocked by anti TGFα antibody (TGF is "transforming growth factor") suggesting that the mitogenic effects of estrogen in this tissue are mediated by TGFα (Nelson et al., 1992 Endocrinology 131, 1657–1664).

Consequently medical intervention in Gynaecology is largely based on steroidal/antisteroidal regulation of the uterus (Yen & Jaffe, 1991 in "Reproductive Endocrinology", Eds. Yen, Jaffe & Benton, Pub. W B Saunders, Philadelphia; Baird, 1993 British Medical Bulletin 49, 73–87). Despite the undoubted success of this approach, no conceptual advances in contraceptive technology have arisen for 20 years, no means identified to improve implantation, no advances made in promoting placental growth and development and no new approaches found to treat benign gynaecological disease (menstrual dysfunction and fibroids).

A number of publications have been made in relation to the use of "gene transfer" in mammals to alter the genotype of at least some cells in a certain tissue or tissues. In particular, it is known to attempt "gene therapy" of humans by the introduction into recipients of nucleic acid sequences, with the aim of overcoming a genetic deficiency in the recipient by the expression of polypeptides encoded by the introduced nucleic acid sequences. Gene therapy trials have been conducted, for example, in which DNA sequences (incorporated within viral vectors) were introduced into the airways of cystic fibrosis patients, so as to alter the phenotype of at least some of the epithelial cells lining the patients' respiratory tract. Thus far, there have been no published attempts to introduce DNA into the mammalian endometrium, despite the availability of suitable techniques therefor.

SUMMARY OF THE INVENTION

In one aspect, the invention provides a method of altering one or more characteristics of at least some of the cells of the reproductive tract of a mammalian individual by the introduction into said cells of a nucleic acid.

In a second aspect the invention provides a composition comprising nucleic acid, for use in altering one or more characteristics of at least some of the cells of the reproductive tract of a mammalian individual.

In a third aspect the invention provides for use of a composition comprising nucleic acid for altering one or more characterstics of at least some of the cells of the reproductive tract of a mammalian individual.

In a fourth aspect the invention provides for use of a composition comprising nucleic acid in the preparation of a substance for altering one or more characteristics of at least some of the cells of the reproductive tract of a mammalian individual.

In a fifth aspect the invention provides a method of making a composition for use in altering one or more characteristics of at least some of the cells of the reproductive tract of a mammalian individual, comprising mixing a nucleic acid with a physiologically acceptable carrier substance.

The present invention can in no way be considered as an obvious extension of genetic therapy techniques already known to be at least partially successful when applied to the lungs of cystic fibrosis patients. Inherited genetic disorders are not thought to be responsible for any of the known diseases of the endometrium, so there would have been no incentive for those skilled in the art to apply gene therapy techniques to the endometrium. Further, the epithelium of the endometrium is of a different type (cuboidal, derived from coelomic epithelium) compared to lung epithelium (which is stratified) and therefore could not have been predicted to behave in an analagous manner. Moreover, at least in primates, there is cyclical shedding of the endometrial epithelium which would tend to cause the loss of any transfected cells. Finally, the inventors have found that there was no transfer of the introduced DNA into the organs of the mother, nor into the placenta of the embryo, either of which might have occurred and could have caused practical difficulties.

Typically the nucleic acid is introduced into a mammalian female (preferably a woman) and, in particular, into the endometrial cells thereof. Desirably the nucleic acid is introduced into the glandular epithelium of the endometrium. The nucleic acid may encode a polypeptide which is already naturally synthesised by the cells into which the nucleic acid is introduced, such that the level of expression of that polypeptide is increased via a gene dosage effect. Alternatively the method can be used to induce the cells to express a polypeptide not previously synthesised in those cells. The polypeptide could, for example, be an "artificial" recombinant polypeptide which does not exist in nature, such as a chimeric polypeptide comprising, wholly or in part, functional domains from two or more different proteins.

The nucleic acid is preferably DNA, but one could seek to introduce RNA (either sense or non-sense strands). An antisense molecule could be used to inhibit or otherwise interfere with the expression of a polypeptide in the cells into which the nucleic acid is introduced. The nucleic acid sequence introduced may be antisense RNA, or may be a DNA sequence directing the synthesis, intracellularly, of antisense RNA. Another way of achieving such inhibition is to introduce into the cells a sequence directing the synthesis of a ribozyme, which will then specifically cleave the mRNA needed to synthesise the polypeptide whose expression is sought to be inhibited.

The present inventors have found that the time of administration of the nucleic acid (relative to the stage of the reproductive cycle) greatly affects the efficiency of uptake of the nucleic acid. The inventors have found that, in general, in order to obtain the optimum degree of uptake of the administered nucleic acid it is necessary for the administration to be made in the period following ovulation, up to and including the day on which there is a peak of progesterone level in the blood. The progesterone level normally peaks at around a similar time to the point at which an embryo, if present in the uterus, could become implanted.

Thus, for example, the inventors have found that maximal uptake of administered DNA by mouse endometrium occurs at day 2–3 in the cycle (with day 1 taken as the day on which a vaginal plug is first detected). In humans, ovulation typically occurs at day 14 of the cycle, and implantation is generally reckoned to occur in the mid-luteal phase (although the exact time is poorly defined in humans).

The nucleic acid may be administered in a naked form, or may be bound or associated with other substances (e.g. liposomes). Conveniently the nucleic acid is introduced into the cells of the recipient mammal by simple transfection (with or without liposomes), which has been found by the present inventors to be surprisingly effective, without the need for the sequence to be introduced within a viral vector. Nevertheless, viral vectors may be desirable, especially those which may be targeted to certain cell types (e.g. as disclosed in WO 93/20221).

The nucleic acid will conveniently be introduced as part of a construct (e.g. a plasmid, cosmid or the like), which construct will advantageously comprise a promoter, operable in a mammal, to cause transcription of at least part of the introduced nucleic acid. The promoter may be constitutive or, more preferably, inducible so as to allow greater control of expression of the introduced sequence.

In one particular method performed in accordance with the invention, introduction of a nucleic acid molecule into the endometrial cells of an individual mammalian female allows for the up- or down-regulation of the fertility of the individual. The invention may particularly be used to provide a method of contraception for companion animals (e.g. cats and dogs) to prevent unwanted litters. In other embodiments the invention provides a method of improving the fertility of livestock species, such as pigs, cattle, sheep and the like.

Preferably the nucleic acid is introduced into the reproductive tract via the vagina, which avoids the need for invasive surgical techniques. However, if necessary, the nucleic acid could be introduced by means of surgical techniques directly into the reproductive tract (e.g. into the uterus). The invention offers the possibility of altering one or more characteristics by the introduction of one or more of a very large number of different nucleic acid sequences.

In one embodiment, the sequence introduced into the reproductive tract cells directs the expression (preferably at high levels) of an effective portion of a cytokine or growth factor (an effective portion is that part of the molecule which retains the biological activity particularly associated with the whole e.g. binding to a specific ligand etc.). Examples of such polypeptides which might be expressed by the introduced sequence include, but are not limited to, the following: interleukins, leukaemia inhibitory factor (LIF), vascular endothelial growth factor (VEGF), epidermal growth factor (EGF), heparin-binding epidermal growth factor (HBEGF), insulin-binding growth factors I and II (IGF-I and IGF-II), amphiregulin, colony stimulating factor (CSF), and tumour necrosis factor (TNF).

In another embodiment the introduced sequence may direct the expression of an effective portion of an antagonist of a cytokine or growth factor, such as the IL-1 receptor antagonist. Advantageously, the antagonist may be a soluble receptor for the cytokine or growth factor. Suitable examples include soluble receptors for the following: transforming growth factor (TGF) $\alpha$, fibroblast growth factor (FGF), platelet-derived growth factor (PDGF), interleukin-6 (IL-6), and VEGF.

In another embodiment the introduced sequence may direct the expression of an effective portion of a polypeptide having an immunological effect. In particular, the polypeptide may possess immunogenic activity, thereby serving to stimulate a local immune response, thus the invention can be used to provide a novel method of immunisation. Advantageously the immunogenic polypeptide will be an antigen from a mucosal pathogen. By virtue of the common mucosal immune system, stimulation of antibody production in the reproductive tract may result in the production of corresponding antibodies at distal mucosal sites, such as the gastro-intestinal tract, the respiratory tract, lachrymal glands and the like. Preferably however the antigen will be one from a pathogen which invades and/or colonises the reproductive tract, typically a pathogen which causes a sexually transmitted disease. Examples include viruses such as HIV, papilloma viruses (e.g. HPV, of various types), chlamydia and bacteria (e.g. *N. gonorrhoea*). Alternatively, the polypeptide having an immunoloigical effect may be an immunoglobulin or effective portion thereof (such as an Fab, Fv, or scFv fragment, or a single chain antibody). The immunoglobulin or effective portion thereof may be directed against a pathogen (such as those mentioned above), or may be directed against some other antigen, such as a steroid or other hormone. Thus immunoglobulins or fragments thereof could be expressed locally to provide protection against disease or to regulate fertilty.

In another embodiment, the introduced sequence may direct the expression of a polypeptide, or an effective portion thereof, which has an effect on menstruation.

In another embodiment the introduced nucleic acid may direct the expression, on the surface of the reproductive tract cells, of an effective portion of a receptor molecule. The receptor could be a receptor for a cytokine, a steroid hormone, or a growth factor (such as the EGF receptor, the TGF$\alpha$ receptor, or the VEGF receptor). A number of receptors are known which are described as "orphan" receptors, in that the ligand which binds to the receptor is unknown. Such orphan receptors are of considerable interest to the pharmaceutical industry, as they may provide targets for novel therapeutic or prophylactic compounds.

Accordingly, in another aspect the invention provides a method of characterising the biological properties of a polypeptide, comprising introducing the sequence encoding the polypeptide to be characterised into the cells of the reproductive tract of a mammal, and assessing the effects of the expressed polypeptide. Preferably the mammal is a laboratory animal, such as a mouse or rat. Conveniently, the polypeptide to be characterised will be an orphan receptor and typically at least part of the characterisation thereof will comprise identification of the ligand therefor. Generally the method will involve the analysis of histological sections taken from the laboratory mammal, and processing thereof by any one of various standard techniques (e.g. histochemical staining, in situ hybridisation, immunological staining etc.).

The present invention thus offers a novel alternative to steroidal regulation of endometrial function (and thus reproductive capacity or fertility) by direct gene transfer in vivo. To achieve this, genetic constructs would be designed to specifically modulate cytokine action. This can be achieved in a variety of ways. For example the cells that produce a secreted cytokine could be prevented from synthesizing the factor by blocking transcription and translation using promoter driven antisense constructs or ribozymes. Alternatively the action of the secreted factor can be blocked by receptor antagonists. Naturally occurring soluble receptors may scavenge and neutralize bioactive ligand thereby acting as competitive receptor antagonists. Alternatively there are natural receptor antagonists, for example IL1Ra (interleukin-1 receptor antagonist). Intraperitoneal administration of this protein blocks blastocyst implantation in the mouse (Simon et al., 1994 cited elsewhere).

There is considerable evidence to show that soluble growth factors secreted by the oviduct and uterine epithelium can control pre-implantation development of the mammalian embryo, by acting directly through receptors expressed on the embryo (Pampfer et al., 1990 In Vitro Cellular and Developmental Biology 26, 944–948). In turn, developing embryos produce growth factors which may act in an autocrine fashion, or on the endometrium to influence its receptivity. For example, in mice, LIF expression (from maternal tissues) is dramatically upregulated in glandular epithelium on day 4, just prior to implantation. LIF is able to act on pre-implantation blastocysts, which express the LIF receptor (LIF-R). This maternal expression of LIF is vital for implantation since in LIF knockout mice, embryos will not implant, although they will do so on transfer to pseudopregnant dams (Stewart et al., 1992 cited elsewhere).

The inventors have now extended this work to humans, and shown by RT-PCR that human embryos express the mRNA encoding the LIF-R, but do not themselves express LIF. LIF acts by binding to a low affinity receptor LIF-R. High affinity binding arises when the LIF/LIF-R complex interacts with the signal transducing accessory protein gp130. Human embryos also contain mRNA encoding this protein (Sharkey et al., 1995 Biology of Reproduction 53, 955–962). The inventors have also shown LIF secretion in human glandular epithelium is regulated by steroids, being maximal in the luteal phase (around the expected time of implantation—Charnock-Jones et al., 1994 cited elsewhere). Furthermore, administration of LIF to human pre-implantation embryos in vitro, has been reported to improve development. All this evidence supports the idea that LIF may be important in human implantation as it is in the mouse. Clearly cytokines may mediate important communication between the embryo in the uterine lumen, and the endometrium (in both directions) The present invention allows the use of gene transfer to disrupt or enhance this communication, leading to novel methods of contraception, or conversely improved implantation.

Most current studies of the paracrine and autocrine regulation of reproductive function are limited to a descriptive analysis by the lack of effective methods to modulate local cytokine/receptor levels. The evidence presented in this application indicates that transfection of uterine epithelium in vitro is feasible. This allows the endometrium to be manipulated experimentally and offers new therapeutic strategies. The work outlined below describes the use of a reporter gene to demonstrate the practicability of in vivo uterine gene transfer. In practice a gene (or other DNA construct), able to alter uterine function, would be used. Examples of these include receptor antagonists (e.g. IL-1Ra, soluble VEGF receptors etc.) natural or modified cytokines and growth factors, protease inhibitors or steroid receptors and a variety of ribozyme and antisense constructs. This work shows that genes can be transferred to the endometrium in vivo and this will find utility in many endometrial (and placental) conditions for example improving implantation in both animals and man, disrupting implantation (i.e. contraception), endometriosis and menorrhagia, hyperplasia and adenocarcinoma.

Using the protocols we have developed the results described below were obtained. They demonstrate that gene constructs can be transferred to the endometrium both in vivo (in mice) and in vitro and that these constructs are transcriptionally (and translationally) active.

The invention will now be further described by way of illustrative example and with reference to the accompanying drawings, in which.

EXAMPLES

Example 1

Mice

Nulliparous mature BALB/cJ mice were housed in a light (14 h light:10 h dark; lights off at 20.00 h) and temperature (22° C.) controlled Small Animal House and fed a mouse and rat diet (Labsure; Christopher Hill Group, Poole, Dorset, UK). They were placed with vasectomized males of the same stock overnight and examined the next morning for the presence of a vaginal plug. Mating was presumed to have occurred at 02.00 h, time 0 and day 1 was counted as the day on which the plug was first detected. Mated females were housed individually prior to experimentation.

Laparotomy was performed using aseptic procedures under Metafane anaesthesia (methoxyfluorane, C-Vet Ltd., Bury St. Edmunds). The uterine horns were exposed by either mid-ventral or bilateral incisions. Injections were made either into the tip of the horn at the tubo-uterine junction or at the base of the horn at the utero-cervical junction. Repeated studies showed that the latter technique provided the best method of administration but for some purposes the former was preferable when it was necessary to minimise disturbance of the reproductive tract.

Injections of liposome/DNA (pcDNA3 construct, +/−β-galactosidase reporter gene), naked DNA or control solutions (25–100 $\mu$l) were performed by insertion of the tip of a flat Stratatip into the base of the horn. Solutions were previously drawn up into the tip by means of a Travesty applicator which was also used to control the slow injection of solutions into the horn.

After injection, the incision was closed using interrupted mattress sutures and the mice allowed to recover in their cages and provided with food and water ad libitum.

Plasmid Constructs

The plasmids described in this application (by way of example) are based on the commercially available vector pcDNA (Catalogue No. V790-20, from Invitrogen, San Diego, Calif., USA). Plasmid pcDNA3, without any reporter gene, was used as a negative control. Experimental plasmids pcDNA3-βgal, pcDNA3-CAT, and pcDNA3-Luc contained the β-galactosidase, chloramphenicol acetyltransferase and luciferase reporter genes respectively. These plasmids contained the following genetic elements: Ampicillin resistance gene, ColE1 original of replication, CMV promoter, [reporter gene], bovine growth hormone polyA addition site, fl origin of replication, SV40 origin of replication, neomycin resistance gene and an SV40 polyA addition site, in operable relationship such that the reporter gene might be expressible in eukaryotic cells upon introduction of the plasmid. Plasmid DNA was purified from $E.\ coli$ by alkaline lysis and further purified using a Qiagen ion exchange column (according to the manufacturer's instructions).

Liposome Preparation

The liposome used was a 3:1 (w/w) lipid formulation of DOPSA (2,3-dioleyloxy-N-[2(sperminecarboxamido) ethyl]-N-N-dimethyl-1-propanaminium trifluoroacetate) and DOPE (dioleoylphosphatidyl ethanolamine) (LipofectAMINE; Gibco BRL Paisley, Scotland). A number of DNA: lipid ratios and different injection volumes were used as shown in table 1. The DNA/liposomes were mixed immediately prior to each experiment. 10 $\mu$l of DNA solution was added to 10 $\mu$l of lipid solution, mixed gently and left for 15 minutes at room temperature. 80 $\mu$l of PBS was then added to give the final concentration of DNA and lipid as shown in table 1. This was then injected in to the uterus of the pseudopregnant mice. (See section above for details of mice and surgery.)

Histochemical Localisation of β-Galactosidase

Animals were killed by carbon dioxide inhalation and uterine horns dissected out, free of fat and mesentery. Each horn was divided into 3 sections with the top and bottom section being snap-frozen in liquid nitrogen, and stored at −70° C. prior to quantification of β-galactosidase content. The middle section of each uterine horn was fixed in 1.25% gluteraldehyde in PBS for 15 minutes, rinsed in PBS twice, and placed in X-gal staining solution (1 mg/ml X-gal, 5 mM $K_3Fe(CN)_6$, 5 mM $K_4Fe(CN)_6$, 2 mM $MgCl_2$, 0.02% NP40, and 0.01% sodium deoxycholate) for 24 hours at room temperature. Sections were then rinsed in PBS/3% DMSO (2×5 minutes), 70% ethanol (3×5 minutes) and placed in 100% ethanol. Tissues were embedded in glycol methacrylate resin and 7 $\mu$m sections were cut and counterstained with neutral red prior to microscopic examination.

Results

Table 1 below shows the various conditions employed and the resulting staining intensity of uterine sections after administration of DNA/liposome complexes. The results shown in the Table demonstrate the criticality of the timing of administration of the plasmid DNA, with administration on day 2 giving the best levels of expression, administration on day 3 giving reasonable levels, but administration on day 4 resulted in very little expression of the reporter gene, presumably because the endometrial cells would not take up the construct at this time point, for reasons that are not entirely clear.

TABLE 1

| Day of administration (autopsy day) | DNA ($\mu$g/ml) | Lipid ($\mu$g/ml) | Injection volume ($\mu$l) | Histochemical staining intensity |
|---|---|---|---|---|
| 2(5) | 2 | 20 | 50 | ++ |
| 3(5) | 2 | 20 | 50 | ++ |
| 4(6) | 2 | 20 | 50 | − |
| 2(6) | 2 | 20 | 50 | +++ |
| 2(5) | 8 | 20 | 20 | ++ |
| 4(6) | 8 | 20 | 50 | − |
| 4(6) | 30 | 20 | 50 | + |
| 4(6) | 2 | 60 | 50 | − |

Staining intensity +++ strong, ++ moderate, + weak, − none

Controls

An uninjected 6-day pseudopregnant mouse gave no uterine staining for β-galactosidase activity.

A pseudopregnant mouse (administration day 2; autopsy day 6) injected with 50 $\mu$l of pcDNA3 minus β-galactosidase (2 $\mu$g/ml) and lipid (20 $\mu$g/ml) gave no uterine staining for β-galactosidase activity.

Figure 1:
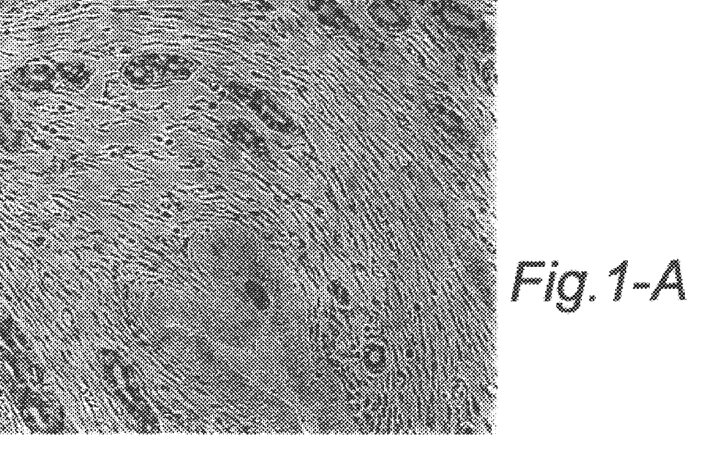
FIGS. 1A and 1B show photomicrographs of histological sections of mouse endometrium transfected with (A) a plasmid construct directing the expression of a β-galactosidase reporter gene, or (B) a similar plasmid lacking the reporter gene. Transfected cells can clearly be identified by the intense dark (blue) staining within the cytoplasm, which is absent in section B.
Figure 2:
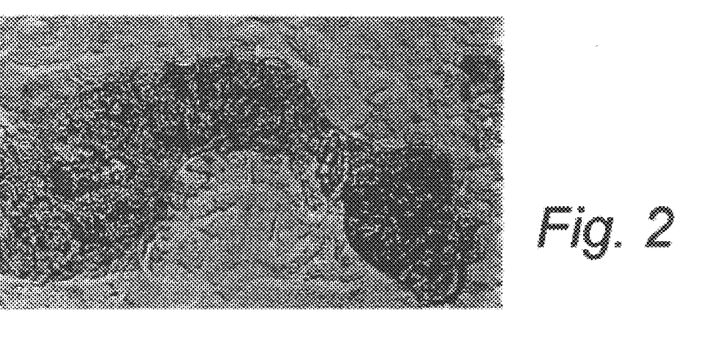
FIG. 2 is a photomicrograph of in vitro human endometrial cells which have been transformed with a the same plasmid as in FIG. 1A—the dark (blue) staining due to expression of the reporter gene is mainly associated with the remaining glandular structure, while the surrounding cells stain more weakly.

Examination of histological sections after staining with X-gal showed that the glandular epithelium was strongly stained and the luminal epithelium was also stained but less strongly. The optimal staining was seen in animals transfected with 2 $\mu$g/ml DNA and 20 $\mu$g/ml lipid in 50 $\mu$l administered on day 2 of pseudopregnancy. FIG. 1$a$ shows a section from such an animal and FIG. 1$b$ a section from a control animal which received (under identical conditions) a plasmid which lacked the β-gal gene.

Example 2

Transfection of Primary Cultures of Human Endometrium

The inventors have also demonstrated that human endometrial epithelial cells can be transfected in vitro at high efficiency.

The same plasmid (pcDNA3, +/−β-galactosidase reporter gene) and lipids as already described were used. Endometrial cells were prepared by the method of Smith and Kelly (Smith et al., 1987 Prostaglandins 34, 553–561). Once the culture were established the following transfection protocol was used. DNA (2 $\mu$g) and liposome (8 $\mu$g) were each diluted in 100 $\mu$l of serum free medium (Opti-MEM1 BRL), mixed and incubated at room temperature for 15 min. Following this a further 800 $\mu$l of Opti-MEM1 was added. The cells (in 24 well plates) were washed with PBS followed by washing with Opti-MEM1. The DNA/liposome mixture (0.5 ml) was then added to the cells and incubated at 37° C. for 3 hr in a $CO_2$ incubator after which 0.5 ml of culture medium containing 20% foetal calf serum was added. Cells were fixed (0.1% gluteraldehyde), rinsed and stained with X-gal 24 h after transfection.

This work shows that genes can be transferred to the endometrium in vivo and this will find utility in many endometrial (and placental) conditions, for example improving implantation in both animals and man, disrupting implantation (i.e. contraception), endometriosis and menorrhagia, hyperplasia and adenocarcinoma.

Additional data were obtained relating to the transfection in vitro of purified human uterine epithelial cells. This complements the in vivo mouse work and shows that similar cells, after minimal time in culture, can be efficiently transfected with the same liposome and DNAs used in vivo.

Example 3

Transfection of Human Endometrial Epithelium In vitro

Human primary epithelial cells from endometrium were isolated and cultured according to the method of Zhang et al., (J Cell Science, 1995; 108:323–331). The cells were plated in standard 6 well tissue culture plates to achieve a density of 50% confluence the next day. The cells were cultured for 5 days, then replated into 24 well plates, at a density of 60,000 cells per well. The next day the cells were transfected with DNA/liposome complexes (DNA/LC). Tnese were prepared as follows:

Transfection Procedure

Apparatus

LipofectAMINE (Gibco Catalogue No. 18324-012), Opti-MEM I (Gibco Catalogue No. 51985-018)

24 well culture dish

Cell culture medium was as described by Zhang et al (cited above).

This consists of DMEM/HEPES, 10% FCS, Endothelial Cell Growth Supplement (Sigma Catalogue No. E-2759), at 30 µg/ml heparin (Sigma Catalogue No. H-3149), at 90 µg/ml, gentamycin (Sigma Catalogue No. G-1272), at 5 µg/ml, and fungizone (Gibco Catalogue No. 15290-018) at 1 µg/ml. Also used were Mg++, Ca++ free PBS and a 2 ml Eppendorf tube.

Two different plasmid constructs were used containing different reporter genes. pcDNA3CAT was obtained from Invitrogen Corporation, and contains a reporter gene encoding the enzyme chloramphenicol acetyl transferase. The second plasmid pcDNA3luc comprised the same vector, but the CAT gene was replaced with the gene encoding the firefly luciferase enzyme. Large scale DNA preparations of the vectors were made using the Qiagen midiprep system. As a negative control, pcDNA3 containing no reporter gene was used.

Preparation of DNA/Liposome Complexes

1) Solution A

Dilute 1 µg of DNA into 100 µl Opti-MEM I in an Eppendorf tube. Use DNA at 1 µg/ml final concentration in the transfection medium.

2) Solution B

Dilute 4 µl of LipofectMINE into 100 µl Opti-MEM I in an Eppendorf tube. Use lipofectAMINE at 8 µg/ml final concentration in the transfection medium.

3) Combine two solutions A and B into a new tube and mix gently.

4) Incubate at room temperature for 15 minutes.

Cell Rinsing

1) Prior to transfection, rinse the cell monolayer roughly three times in FRESH PBS without serum.

2) Re-rinse the cells monolayer twice with Opti-MEM I.

Transfection

1) Add 800 µl (total 1.0 ml) of Opti-MEM to each tube containing the DNA-lipid mixture. Final DNA concentration 1 µg/ml, and lipofectAMINE concentration 8 µg/ml.

2) Remove the Opti-MEM I in the cell monolayer.

3) Mix DNA/LC mixture gently and overlay the diluted complex solution onto the washed cells. 0.5 ml/24 well.

4) Incubate the cell monolayer for 3 hrs at 37° C. in a $CO_2$ incubator.

Further Cell Culture 1) 3 hrs later, remove transfection mixture, and add 2 mls of the Zhang medium to each well, and culture further.

Ouantitative Assay 24 to 48 hours after transfection, the cells were extracted, and assayed for CAT or luciferase reporter activity, as appropriate.

1. Rinse cells three times in PBS.
2. Extract cells with 300 microliters of Lysis buffer (Promega Catalogue No. E-3871), scraping cells off thoroughly into Eppendorf tube.
3. Freeze extract rapidly at −70° C., and store until assay.
4. To assay, thaw extracts and centrifuge at 13,000 g for 5 minutes.
5. Repeat freeze/thaw/spin cycle once more.
6. Assay luciferase reporter gene activity using Luciferase assay kit from Tropix (Catalogue No. BC100L). Use 40 µl of each extract per tube.
7. CAT reporter gene activity was assayed using the Quan-t-CAT kit from Amersham (Catalogue No. TRK 1012).

Results

Primary endometrial epithelial cells were transfected in 24 well plates as described above. Transfections were performed on triplicate wells with pcDNA3 (as control), pcDNACAT, and pcDNA3LUC. After 48 hours the cells were harvested and assayed for luciferase or CAT activity.

The CAT enzyme catalyses the transfer of acetyl groups from acetyl coenzyme A to chloramphenicol. Use of tritiated acetyl coA results in transfer of radiolabel to chloramphenicol. The CAT activity in a sample is directly proportional to the amount of tritiated chloramphenicol produced. Results are therefore expressed in cpm per tube. A standard curve can be produced using lysis buffer containing known amounts of purified CAT.

Figure 3:
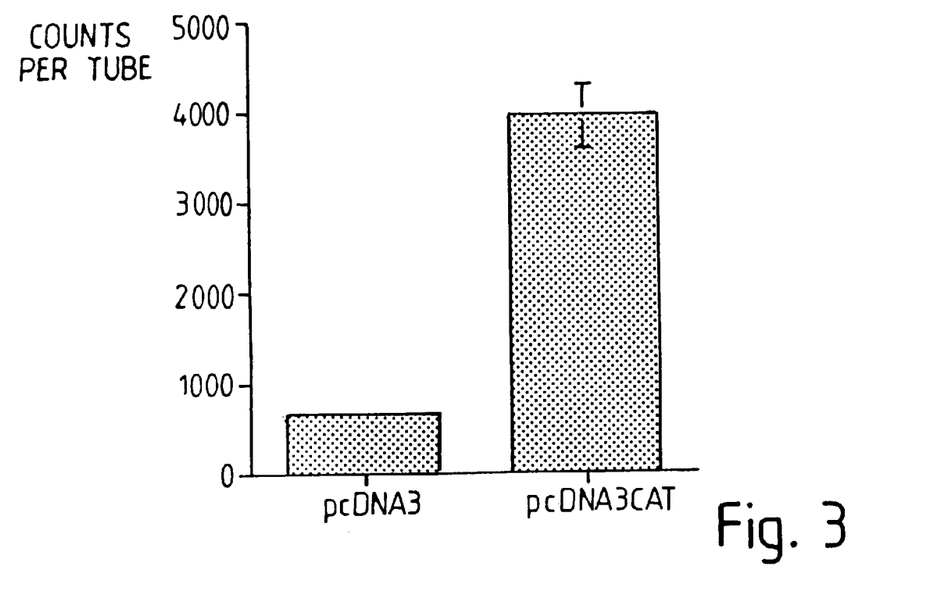
FIG. 3 is a bar chart showing the results of a CAT assay (in counts per tube) for endometrial cells successfully transfected with a gene encoding chloramphenicol acetyltransferase (pcDNA3CAT) compared to cells transfected with a control plasmid (pcDNA3)

The results are shown in FIG. 3, which is a bar chart showing the mean±sem for triplicate determinations for a typical experiment. The results in numerical form were as shown below, with CAT activity in the cells treated with pcDNA3CAT about 6 fold higher than the control samples, demonstrating successful transfection of the endometrial cells.

|  | pcDNA3 | pcDNA3CAT |
|---|---|---|
|  | 710 | 4480 |
|  | 616 | 4134 |
|  | 662 | 3234 |
| mean | 662 ± 271 | 3951 ± 372 |

In the assay for luciferase, the cell extract containing luciferase is mixed with its substrate luciferin, resulting in the emission of light. The light signal intensity is proportional to the luciferase enzyme present in the extract, and can be measured by a luminometer. Initial results are given in relative light units.

Figure 4:
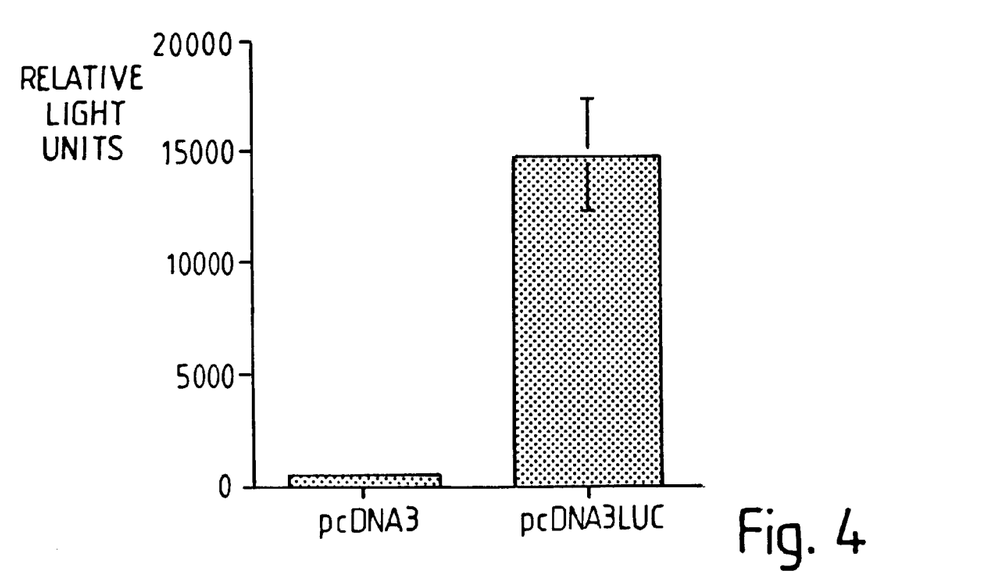
FIG. 4 is a bar chart showing the results of a luciferase assay (in relative light units) for endometrial cells successfully transfected with a gene encoding luciferase (pcDNA3LUC) compared to cells transfected with a control plasmid (pcDNA3).

Results are shown in FIG. 4, which is a bar chart illustrating the mean±sem for triplicate determinations for a typical experiment. The results in numerical form were as shown below. The signal from cells treated with pcDNA3LUC was over 30 fold higher than the background signal of the control samples, again demonstrating successful transfection of the endometrial cells.

Examples of Possible Applications of Endometrial Gene Transfer

At least seven different types of gene construct could be transfected into the endometrium to achieve a variety of different effects. Each of these different types will be described in turn.

1) Over-expression of Cytokines and Growth Factors

These are conceptually the simplest types of constructs in that they will be designed to over-express either a cytokine or a growth factor in the uterine epithelial cells. Examples of suitable cDNAs for such over-expression include those encoding LIF, VEGF, EGF, CSF, TNF, Amphiregulin, and a variety of interleukins and colony stimulating factors. These have been shown to be expressed naturally in the endometrium and are thought to be important in regulating endometrial function. (Stewart et al, 1992, Nature, 359, 76–79; Charnock-Jones et al, 1994, Journal of Reproduction and Fertility, 101, 421–426; Charnock-Jones et al, 1993, Biology of Reproduction, 48, 1120–1128; Das et al, 1995, Molecular Endocrinology, 9, 691-; Tabibzadeh (1994, Human Reproduction Update, 9, 947–967) has published an extensive review of this field). These agents each affect different aspects of reproductive function including implantation, blood vessel development and leukocyte biology. Therefore possible indications for the administration of such constructs would be where one wished to improve fertility, particularly in livestock species, or prevent conception of humans and their companion animals, and also to treat a variety of menstrual disorders in humans.

An Example of an Experiment Designed to Improve Fertility of Livestock

It has been shown that LIF is essential for the process of implantation (Stewart et al, 1992 cited above). This factor is produced by the endometrium at the time of implantation. It is therefore possible that in species where the rates of embryonic loss are high, increasing the levels of LIF expression from the endometrium at the time of implantation could reduce these rates of loss. Therefore, the transfection of a gene construct designed to direct the synthesis of LIF from the endometrium at the time of implantation could improve fertility rates in such species. Constructs transfected into the endometrium would need to contain appropriate regulatory sequences to ensure that the LIF protein was produced at the appropriate time. It is likely that this could be achieved by using the promoter from the LIF gene from the species in question.

Treatments designed to alleviate menstrual dysfunction in women can also be envisaged using endometrium gene transfer. An example of this would be to alter the blood vessel development within the endometrium by transfection of gene encoding angiogenic growth factors, for example VEGF. A local increase in VEGF production might be expected to enhance capillary growth and therefore may promote endometrial thickening. Equally, increased levels of VEGF may facilitate the repair of capillaries after menstruation and thus alter bleeding patterns of patients treated with this type of construct.

2) Over-expression of Receptors

Increasing the number and type of receptors expressed by the uterine epithelium would be anticipated to have significant biological consequences. The types of receptors one may wish to over express include, but are not limited to, growth factor and cytokine receptors for e.g. EGF, TGFα, VEGF and a variety of colony stimulating factors and interleukins. Steroid hormone receptors are also suitable for expression in the epithelial cells. Such transfection would be expected to be useful where one wishes to improve fertility, prevent conception, treat menstrual disorder and also to elucidate the function of orphan receptors (orphan receptors are receptors where the ligand is currently unidentified). Orphan receptors represent an area of great interest to the pharmaceutical industry, since characterisation of the ligand may well lead to generation of new drugs.

It is becoming increasingly recognized that the development of the endometrium is a complex process mediated by an interaction of many cytokines and their receptors and that the stimulatory effects of ovarian steroids are frequently mediated through these cytokines. In particular, it has been shown (Nelson et al, 1992, Endocrinology, 131, 1657–1644) that TGFα is a potential mediator of oestrogen action in the mouse uterus. Therefore transfection of constructs directing synthesis of this factor might be expected to promote endometrial growth, and therefore might enhance fertility in situations where the endometrium had not developed adequately. Similarly, this factor might be anticipated to promote epithelial surface repair after menstruation, and therefore be useful in the treatment of menorrhagia.

There are several members of the steroid hormone receptor superfamily for which the ligand is currently unknown. Transfection of such cDNAs into the endometrium could be of great benefit in elucidating the biological function of these receptors, and therefore may find application in the search for new pharmaceutical agents which act upon these receptors, (Evans 1988, Science 240, 889–895).

3) Transfection of Constructs Designed to Block or Prevent the Action of Cytokine Growth Factors and Other Hormones The transfection of natural antagonists to cytokine and growth factors opens the possibility for modulating endometrial function. An example of such antagonists would be the interleukin 1 receptor antagonist (Hannum et al, 1990 Nature 343, 336). Administration of this protein has been shown to block pregnancy in mice (Simon et al, 1994 Endocrinology 134, 521–528). Other natural antagonists of cytokines and growth factors include the natural soluble receptors. Soluble receptors have been described in a variety of growth factor/cytokine systems. For example TNF (Engelmann et al, 1990, J. Biol. Chem. 265, 14497–14504), FGF (Givol et al, 1992, FASEB Journal, 6, 3362–3369), PDGF (Tiesman & Hart, 1993, J. Biol. Chem. 268, 9621–9628) and IL-6 (Novick et al, 1989, J. Exp. Med. 170, 1409–1414). The common feature is that the extracellular ligand binding domain of the receptor is released from the cell as a freely soluble factor. This is achieved either by proteolysis or by alternative splicing which generates a truncated protein molecule lacking the transmembrane and intracellular domains. Kendall and Thomas (1993, Proc. Natl. Acad. Sci. USA, 90, 10705–10709) described a soluble variant of the VEGF receptor fit. This protein was able to block the action of VEGF in vitro. We have isolated three further cDNAs encoding additional soluble variants (see PCT/GB95/01213). The use of these natural agents has several advantages over other antagonists (for example anti-VEGF antibodies). Since they occur naturally in the body one would anticipate that they would not elicit an immune response and should be well tolerated. Also, since they are derived from the membrane bound receptor, the binding characteristics will be very similar and thus will compete very effectively for the ligand. It is possible that other soluble receptors exist naturally or that they could be engineered in vitro. It is also likely that if the ligand binding domain from a member of the steroid hormone receptor family was expressed, it could act as a dominant negative receptor in that it would compete for the ligand if expressed within the cell at high enough levels. Attentively, a nonactivating but DNA binding "receptor" could be used to block gene transcription. This application would be useful for antagonizing the action on natural steroids including those which are the as yet unidentified ligands for orphan receptors (Pemrick et al. 1994 Leukemia 8, 1797–1806). Signalling deficient receptors from the seven transmembrane domain receptor family could also be engineered and transfected.

The soluble interleukin-1 receptor antagonist (Eisenberg et al, 1990 Nature 343, 341) has been shown to antagonize the actions of IL-1 in vivo (Simon et al, 1994 Endocrinology 134, 521–528). Thus transfection of the endometrium with a cDNA construct designed to direct the synthesis of antagonist would be expected to block pregnancy in mice.

Other factors likely to antaponise growth factor or cytokine action include soluble variants of natural receptors, for example the soluble variant of the VEGF receptor for flt has been described by Kendall & Thomas (1993, cited above) and also by Boocock et al (1995 J. Natl. Cancer Ins. 87, 506–516). Local production of such factors would be expected to antagonise the actions of VEGF and may lead to useful therapeutic use in situations where there is hyperproliferation of endothelial cells, for example in a variety of menstrual disorders where it is desirable to reduce the capillary density in the endometrium. This would include malignant disease.

4) Use of Antisense Methods to Prevent Local Production of a Specific Protein (or Enzyme)

An alternative approach to block the action of cytokines, growth factors and hormones would be to use antisense or ribozyme technology to block either the production of the ligands or the production of the receptors in the appropriate cells (James, 1991 Antiviral Chemistry and Chemotherapy, 2 191–214; Albert & Morris, 1994 Trends in Pharmacological Sciences 15, 250–254).

Antisense technology relies on the binding of a so-called antisense oligonucleotide or polynucleotide to a cellular mRNA. This binding prevents the translation of this mRNA, and therefore reduces the amount of the appropriate protein produced by the cell. Synthetic oligonucleotides or polyribonucleotides have both been used successfully for this approach. Liposome mediated transfection of oligonucleotides or liposome mediated transfection of DNA constructs which direct the synthesis of longer antisense polyribonucleotides would be expected specifically and selectively to reduce protein reduction by the transfected cells. Ribozymes also prevent protein production by selectively cleaving the RNA that encodes the specific protein in question. These too can be transfected in as polyribonucleotides or as DNA constructs which direct the synthesis of such polynucleotides (for reviews see James 1991, and Albert & Morris 1994, both cited above). An example of such a use of an antisense ribozyme to prevent fertility would be as follows. It has already been shown that LIF is essential for the process of implantation in the mammalian pregnancy (Stewart et al, 1992, cited previously). Therefore the transfection of either oligonucleotides or DNA constructs directing the synthesis of antisense polyribonucleotides, or ribozymes directed against the LIF mRNA, would be expected to prevent the synthesis of this factor. The lack of this factor should then lead to a failure of implantation and therefore conception would be blocked.

A similar approach could be used to block the production of angiogenic growth factors, for example VEGF, which would prevent the proliferation of endothelial cells required for tumour growth. Therefore this type of therapy might be particularly advantageous where malignant disease is being treated.

5) Local Production of Immunoglobulins and Fragments Thereof

It is possible using modern recombinant DNA technology to generate single chain antibodies which have nearly identical binding characteristics to the entire monoclonal antibody from which they were derived. Such single chain antibodies have successfully been expressed in bacteria (He et al, 1995 Immunology 84, 662–668). It is possible in principle to engineer a construct which will direct the expression of a single chain antibody and express this in epithelial cells. If this was carried out in the endometrium in vivo one would anticipate that single chain antibodies directed against a steroid hormone would bind to the steroid and prevent its action in the epithelial cells. An example of such an antibody would be the single chain antibody derived from the antiprogesterone monoclonal antibody DB3 (He et al, 1995, cited above). If this antibody were secreted into the uterine lumen it would also bind progesterone and may have actions elsewhere in the uterine compartment. Antibody directed against growth factors and cytokines which are known to be active in the endometrium could similarly block their function if produced locally in this manner.

An additional application for locally produced single chain antibodies would be in preventing or treating sexually transmitted diseases. In this situation antibodies directed against the agent in question (for example papilloma virus, HIV, chlamydia) would be secreted into the uterine lumen and prevent infection by the agent in question. Antibodies directed against sperm or oocyte antigens could be envisaged to play a role in contraception.

6) Active Immunization for Achieving Mucosal Immunity

An additional method which could be used to achieve local immunity would be to design constructs which would direct the secretion of an antigen into the lumen. This would elicit a local immune response and thus site specific mucosal immunity would be achieved. It has been known for many years (Howe, 1967 Journal of Reproduction and Fertility 13, 563–566) that the uterine lumen contains many leukocytes. It is possible that antigen produced by transfected endometrial cells taken up by these leukocytes and subsequently presented to elicit a mucosal immune response. Delivery of antigens to the intestinal lumen has resulted in such immunity and in some instances has been shown to be very effective (for example vaccination against poliomyelitis).

7) Blocking Pathogen Attachment Sites

Attachment of pathogens to mucosal surfaces is frequently an essential prerequisite to the establishment of infection. Blocking attachment of the pathogens to these sites may thus present a method of protecting humans or animals against disease, particularly sexually transmitted diseases. This applies not only to bacterial pathogens (such as certain pathogenic strains of *E. coli*, and *N. gonorrhoea*), but also to viral pathogens. Many viruses when infecting a cell attach by a cell surface "receptor". The local production of soluble receptors may be expected to compete with the cell surface molecules and thus prevent viral infection. Equally the saturation of the cell surface receptors with viral mimics (which act like the viral "lizand") might also block infection, as might local production of specific immunoglobulins or effective binding portions thereof.

What is claimed is:

1. A method of transfecting uterine epithelial cells of a human in vivo comprising:
   a) providing a composition comprising a vector comprising a nucleic acid sequence encoding a protein operatively linked to a promoter;
   b) administering the composition into the lumen of a uterus in a human in vivo, wherein the composition is administered following ovulation of the human but before or during the peak in the level of progesterone in the blood of the human within the same reproductive cycle; and c) obtaining detectable expression of the protein in at least some uterine epithelial cells of the human.

2. The method of claim 1, wherein the uterine epithelial cells are glandular epithelial cells.

3. The method of claim 1, wherein the composition further comprises a liposome.

4. The method of claim 1, wherein the vector is a plasmid.

5. The method of claim 4, wherein the plasmid is pcDNA3.

6. The method of claim 1, wherein the promoter is an inducible promoter.

7. The method of claim 1, wherein the promoter is the CMV promoter.

8. A method of transfecting uterine endometrial cells of a mammal in vivo comprising:
   a) providing a composition comprising a vector comprising a nucleic acid sequence encoding a protein operatively linked to a promoter;
   b) administering the composition into the lumen of a uterus in a mammal in vivo, wherein the composition is administered following ovulation of the mammal but before or during the peak in the level of progesterone in the blood of the mammal within the same reproductive cycle; and
   c) obtaining detectable expression of the protein in at least some uterine endometrial cells of the mammal.

9. The method of claim 8, wherein the promoter is the CMV promoter.

10. A method of transfecting uterine epithelial cells of a mammal in vivo comprising:
    a) providing a composition comprising a plasmid comprising a nucleic acid sequence encoding a protein operatively linked to a promoter, wherein the concentration of the plasmid is at least 1 $\mu$g/ml;
    b) administering the composition into the lumen of a uterus in a mammal in vivo, wherein the composition is administered following ovulation of the mammal but before or during the peak in the level of progesterone in the blood of the mammal within the same reproductive cycle; and
    c) obtaining detectable expression of the protein in at least some uterine endometrial cells of the mammal.

* * * * *